United States Patent
Webster

(10) Patent No.: US 11,415,551 B2
(45) Date of Patent: Aug. 16, 2022

(54) RESONATOR FOR DETECTING SINGLE MOLECULE BINDING

(71) Applicant: QORVO Biotechnologies, LLC, Plymouth, MN (US)

(72) Inventor: James Webster, Minnetonka, MN (US)

(73) Assignee: Qorvo Biotechnologies, LLC, Plymouth, MN (US)

( * ) Notice: Subject to any disclaimer, the term of this patent is extended or adjusted under 35 U.S.C. 154(b) by 747 days.

(21) Appl. No.: 16/095,963

(22) PCT Filed: Apr. 25, 2017

(86) PCT No.: PCT/US2017/029311
§ 371 (c)(1),
(2) Date: Oct. 24, 2018

(87) PCT Pub. No.: WO2017/189512
PCT Pub. Date: Nov. 2, 2017

(65) Prior Publication Data
US 2019/0137449 A1 May 9, 2019

Related U.S. Application Data

(60) Provisional application No. 62/327,749, filed on Apr. 26, 2016.

(51) Int. Cl.
*G01H 13/00* (2006.01)
*G01N 5/02* (2006.01)
(Continued)

(52) U.S. Cl.
CPC .............. *G01N 29/022* (2013.01); *G01H 1/06* (2013.01); *G01H 13/00* (2013.01); *G01N 5/02* (2013.01);
(Continued)

(58) Field of Classification Search
CPC .... G01N 5/02; G01N 29/2443; G01N 29/036; G01N 33/557; G01N 29/022;
(Continued)

(56) References Cited

U.S. PATENT DOCUMENTS

| 5,932,953 A | 8/1999 | Drees et al. |
| 7,871,569 B2 * | 1/2011 | Zhang .................. G01N 29/348 422/68.1 |

(Continued)

FOREIGN PATENT DOCUMENTS

WO WO 2014/143680 A1 9/2014

OTHER PUBLICATIONS

International Patent Application No. PCT/US2017/029311, filed Apr. 25, 2017, International Preliminary Report on Patentability dated Oct. 30, 2018, 6 pages.

(Continued)

*Primary Examiner* — Jacques M Saint Surin
(74) *Attorney, Agent, or Firm* — Mueting Raasch Group

(57) ABSTRACT

Various embodiments of an apparatus for measuring binding kinetics of an interaction of an analyte material present in a fluid sample are disclosed. The apparatus includes a sensing resonator having at least one binding site for the analyte material; actuation circuitry adapted to drive the sensing resonator into an oscillating motion; measurement circuitry coupled to the sensing resonator and adapted to measure an output signal of the sensing resonator representing resonance characteristics of the oscillating motion of the sensing resonator; and a controller coupled to the actuation and measurement circuitry, wherein the controller is adapted to detect an individual binding event between the at least one binding site and a molecule of the analyte material.

13 Claims, 4 Drawing Sheets

(51) Int. Cl.
*G01N 29/24* (2006.01)
*G01H 1/06* (2006.01)
*G01N 29/036* (2006.01)
*G01N 33/557* (2006.01)
*G01N 29/02* (2006.01)

(52) U.S. Cl.
CPC ....... *G01N 29/036* (2013.01); *G01N 29/2443* (2013.01); *G01N 33/557* (2013.01); *G01N 2291/0255* (2013.01); *G01N 2291/0256* (2013.01); *G01N 2291/02466* (2013.01); *G01N 2291/0426* (2013.01); *G01N 2291/106* (2013.01)

(58) Field of Classification Search
CPC ... G01N 2291/0256; G01N 2291/0426; G01N 2291/02466; G01N 2291/106; G01N 2291/0255; G01H 1/06; G01H 13/00
USPC ........................................................ 436/517
See application file for complete search history.

(56) References Cited

U.S. PATENT DOCUMENTS

| | | | |
|---|---|---|---|
| 8,409,875 B2 | 4/2013 | Johal et al. | |
| 10,451,618 B2 * | 10/2019 | Tischer | G01N 29/30 |
| 10,812,045 B2 * | 10/2020 | Rivas | H03H 9/17 |
| 2003/0215865 A1 | 11/2003 | Mayer et al. | |
| 2011/0269649 A1 | 11/2011 | Roukes et al. | |
| 2012/0190131 A1 | 7/2012 | Novotny | |
| 2014/0127826 A1 * | 5/2014 | Johal | G01N 33/54373 436/501 |
| 2014/0154697 A1 * | 6/2014 | Johal | G01N 33/557 435/7.1 |
| 2015/0011428 A1 | 1/2015 | Cable et al. | |

OTHER PUBLICATIONS

International Patent Application No. PCT/US2017/029311, filed Apr. 25, 2017, International Search Report and Written Opinion dated Jul. 7, 2017, 8 pages.
Esser, et al., "Principles in Adsorption to Polystyrene", *Technical Bulletin: 06a (D19559)*, 2010, Thermo Fisher Scientific Inc., Waltham, Massachusetts, 6 pages.
Lee, et al., "Toward Attograni Mass Measurements in Solution with Suspended Nanochannel Resonators", *2010 Nano Lett.*, 10:2537-2542.
"Sauerbrey equation." Wikipedia [online] [retrieved on Feb. 11, 2019]. Retrieved from the Internet at <URL:https://en.wikipedia.org/wiki/Sauerbrey_equation>, 2 pages.

* cited by examiner

RESONATOR FOR DETECTING SINGLE MOLECULE BINDING

RELATED APPLICATIONS

This application is the § 371 U.S. National Stage of International Application No. PCT/US2017/029311, filed on Apr. 25, 2017, which claims the benefit of U.S. Provisional Patent Application No. 62/327,749, filed on Apr. 26, 2016, the disclosures of which are hereby incorporated herein by reference in their entireties to the extent that it does not conflict with the disclosure presented herein.

BACKGROUND

Piezoelectric devices such as thin film bulk acoustic wave (BAW) resonators and similar technologies like quartz crystal microbalances (QCM) have been employed as mass detectors for some time. One application of piezoelectric resonators is in detecting very small quantities of materials. Piezoelectric resonators used as sensors in such applications are sometimes called "micro-balances." A piezoelectric resonator is typically constructed as a thin, planar layer of crystalline or polycrystalline piezoelectric material sandwiched between two electrode layers. When used as a sensor, the resonator is exposed to the material being detected to allow the material to bind on a surface of the resonator.

One conventional way of detecting the amount of the material bound on the surface of a sensing resonator is to operate the resonator at its resonant frequency in an oscillator circuit. As the material being detected binds on the resonator surface, the oscillation frequency of the resonator is reduced. The change in the oscillation frequency of the resonator, presumably caused by the binding of the material on the resonator surface, is measured and used to calculate the amount of the material bound on the resonator or the rate at which the material accumulates on the resonator surface.

The sensitivity of a piezoelectric resonator in air as a material sensor is theoretically proportional to the square of the resonance frequency. Thus, the sensitivities of material sensors based on the popular quartz crystal resonators are limited by their relatively low oscillating frequencies, which typically range from several MHz to about 100 MHz. The development of thin-film resonator (TFR) technology can potentially produce sensors with significantly improved sensitivities. A thin-film resonator is formed by depositing a thin film of piezoelectric material, such as AlN or ZnO, on a substrate. Due to the small thickness of the piezoelectric layer in a thin-film resonator, which is on the order of several microns, the resonant frequency of the thin-film resonator is on the order of 1 GHz. The high resonant frequencies and the corresponding high sensitivities make thin-film resonators useful for material sensing applications. However, mass sensitivity of even thin-film resonators may be limited for detection of certain analytes, such as biological analytes.

The use of piezoelectric resonator sensors in immunoassays has been described previously. In general, piezoelectric based immunoassays, in which mass change is attributable to the immunological reaction between an antigen and an antibody, can in some circumstances suffer from poor sensitivity and poor detection limit.

SUMMARY

In one aspect, the present disclosure provides an apparatus for measuring binding kinetics of an interaction of an analyte material present in a fluid sample. The apparatus includes a sensing resonator having at least one binding site for the analyte material; actuation circuitry adapted to drive the sensing resonator into an oscillating motion; measurement circuitry coupled to the sensing resonator and adapted to measure an output signal of the sensing resonator representing resonance characteristics of the oscillating motion of the sensing resonator; and a controller coupled to the actuation and measurement circuitry, where the controller is adapted to detect an individual binding event between the at least one binding site and a molecule of the analyte material.

In another aspect, the present disclosure provides a method carried out by an apparatus for measuring binding kinetics of an interaction of an analyte material present in a fluid sample. The method includes contacting a sensing resonator with the fluid sample, where the sensing resonator includes at least one binding site for the analyte material; actuating the sensing resonator into an oscillating motion; measuring an output signal representing resonance characteristics of the oscillating motion of the sensing resonator; and detecting an individual binding event between the at least one binding site and a molecule of the analyte material.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

This disclosure generally relates to, among other things, methods, devices, sensors, and systems for detecting an analyte. The methods, devices, sensors, and systems use a thin film bulk acoustic wave (BAW) resonator that measures a change in frequency or phase of the resonator caused by the binding of the analyte on a surface of the resonator. An input electrical signal having a phase and having a frequency within a resonance band of the piezoelectric resonator, which in the case of some embodiments of the present disclosure may be about 500 MHz or greater, such as about 1.5 GHz or greater, is coupled to and transmitted through the resonator to generate an output electrical signal which is frequency-shifted or phase-shifted from the input signal due to binding, deposition, etc. of material being detected on the resonator surface. The output electrical signal received from the piezoelectric resonator is analyzed to determine the change in frequency or phase caused by the binding of analyte on the resonator surface. The measured change in frequency or phase provides quantitative information regarding the analyte (or tag-linked analyte molecule) bound to the resonator surface.

Sensors, Devices and Systems

The sensors disclosed herein include at least one thin film resonator sensor, such as a thin film bulk acoustic wave (BAW) resonator sensor. A BAW sensor includes a piezoelectric layer, or piezoelectric substrate, and input and output transducers. BAW sensors are small sensors, making the technology suitable for use in handheld devices. Accordingly, a handheld device for detecting target analytes comprising a sensor described herein is contemplated.

Figure 1A:
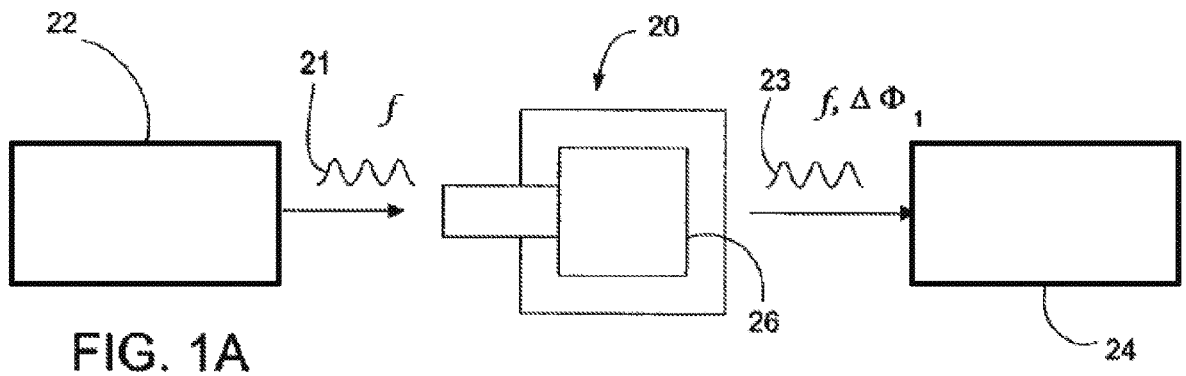
FIGS. 1A-1C are schematic diagrams illustrating the operational principles of embodiments of thin film bulk acoustic wave (BAW) resonator sensing devices.
Figure 1B:
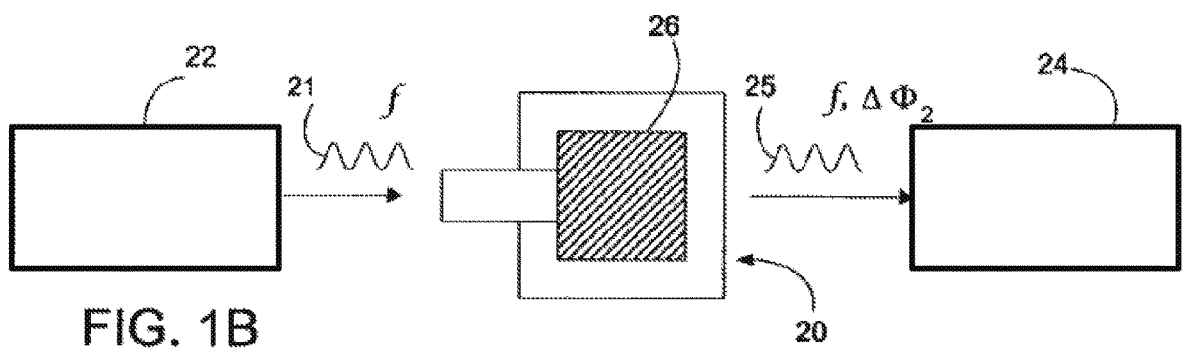

Turning now to the drawings with reference to FIGS. 1A and 1B, general operating principles of an embodiment of a bulk-acoustic wave piezoelectric resonator 20 used as a sensor to detect an analyte are shown. The resonator 20 typically includes a planar layer of piezoelectric material bounded on opposite sides by two respective metal layers that form the electrodes of the resonator. The two surfaces of the resonator are free to undergo vibrational movement when the resonator is driven by a signal within the resonance band of the resonator. When the resonator is used as a sensor, at least one of its surfaces is adapted to provide binding sites for the material being detected. The binding of the material on the surface of the resonator alters the resonant characteristics of the resonator, and the changes in the resonant characteristics are detected and interpreted to provide quantitative information regarding the material being detected.

By way of example, such quantitative information may be obtained by detecting a change in the insertion or reflection coefficient phase shift of the resonator caused by the binding of the material being detected on the surface of the resonator. Such sensors differ from those that operate the resonator as an oscillator and monitor changes in the oscillation frequency. Rather such sensors insert the resonator in the path of a signal of a pre-selected frequency and monitor the variation of the insertion or reflection coefficient phase shift caused by the binding of the material being detected on the resonator surface. Of course, sensors that monitor changes in oscillation frequency may also be employed in accordance with the methods described herein.

In more detail, FIG. 1A shows the resonator 20 before the material being detected is bound to its surface 26. The depicted resonator 20 is electrically coupled to a signal source 22, which provides an input electrical signal 21 having a frequency f within the resonance band of the resonator. The input electrical signal is coupled to the resonator 20 and transmitted through the resonator to provide an output electrical signal 23. In the depicted embodiment, the output electrical signal 23 is at the same frequency as the input signal 21, but differs in phase from the input signal by a phase shift $\Delta\Phi_1$, which depends on the piezoelectric properties and physical dimensions of the resonator. The output signal 23 is coupled to a phase detector 24 that provides a phase signal related to the insertion phase shift.

FIG. 1B shows the sensing resonator 20 with the material being detected bound on its surface 26.

The same input signal is coupled to the resonator 20. Because the resonant characteristics of the resonator are altered by the binding of the material as a perturbation, the insertion phase shift of the output signal 25 is changed to $\Delta\Phi_2$. The change in insertion phase shift caused by the binding of the material is detected by the phase detector 24. The measured phase shift change is related to the amount of the material bound on the surface of the resonator.

Figure 1C:
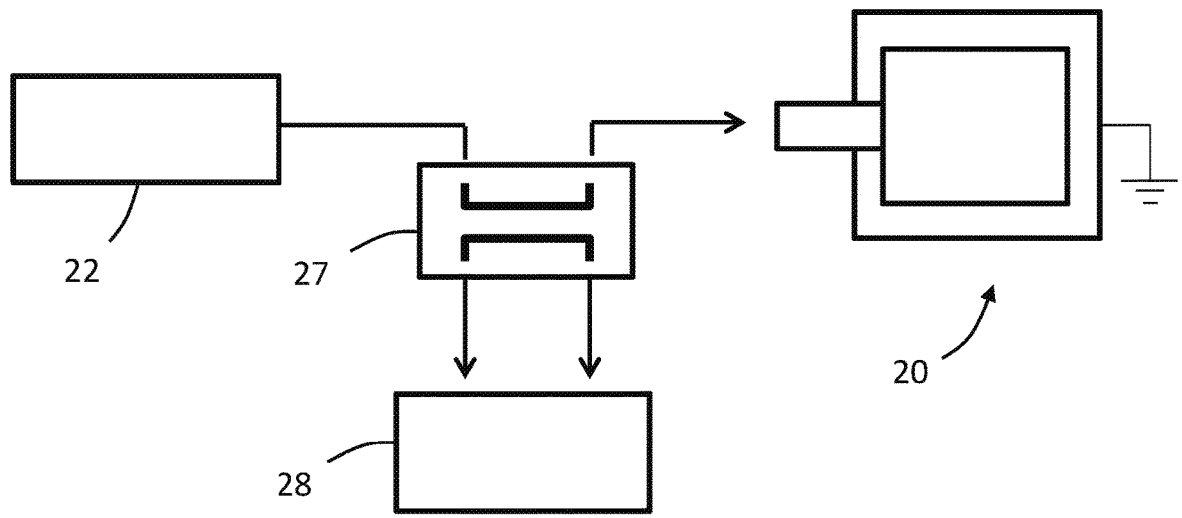

FIG. 1C shows an alternative to measuring the insertion phase of the resonator. A directional coupler 27 is added between the signal source 22 and the resonator 20 with the opposite electrode grounded. A phase detector 28 is configured to measure the phase shift of the reflection coefficient as a result of material binding to the resonator surface.

Other BAW phase-shift sensors that may be employed with the aspects described herein include those described in, for example, U.S. Pat. No. 8,409,875, entitled RESONATOR OPERATING FREQUENCY OPTIMIZATION FOR PHASE-SHIFT DETECTION SENSORS, which patent is hereby incorporated herein by reference in its entirety to the extent that it does not conflict with the disclosure presented herein. For example, sensor apparatuses may include (i) a sensing resonator including binding sites for an analyte; (ii) actuation circuitry configured to drive the sensing resonator in an oscillating motion; (iii) measurement circuitry arranged to be coupled to the sensing resonator and configured to measure one or more resonator output signals representing resonance characteristics of the oscillating motion of the sensing resonator; and (iv) a controller operatively coupled with the actuation and measurement circuitry. The controller can be interfaced with data storage containing instructions that, when executed, cause the controller to adjust the frequency at which the actuation circuitry drives the sensing resonator to maintain a resonance point of the sensing resonator. Accordingly, sensing may be accomplished by actuating the BAW sensor into an oscillating motion; measuring one or more resonator output signals representing resonance characteristics of the oscillating motion of the BAW sensor; and adjusting the actuation frequency of the sensing resonator to maintain a resonance point of the BAW sensor.

Such phase detection approaches can be advantageously used with piezoelectric resonators of different resonant frequencies.

In various embodiments, BAW sensors for use with the methods, devices, and system described herein have resonance frequencies of about 500 MHz or greater, such as about 700 MHz or greater, about 900 MHz or greater, about 1 MHz or greater, about 1.5 GHz or greater, about 1.8 GH or greater, about 2 GHz or greater, about 2.2 GHz or greater, about 2.5 GHz or greater, about 3 GHZ or greater, or about 5 GHZ or greater can provide enhanced sensitivity. In embodiments, the BAW sensors have resonance frequencies of from about 500 MHz to about 5 GHz, such as from about 900 MHz to about 3 GHz, or from about 1.5 GHz to about 2.5 GHz. Some of such frequencies are substantially higher than frequencies of previously described piezoelectric resonators.

The sensing resonators described herein are thin-film resonators. Thin film resonators include a thin layer of piezoelectric material deposited on a substrate, rather than using, for example, AT-cut quartz. The piezoelectric films typically have a thickness of less than about 5 micrometers, such as less than about 2 micrometers, and may have thicknesses of less than about 100 nanometers. Thin-film resonators are generally preferred because of their high resonance frequencies and the theoretically higher sensitivities. Depending on the applications, a thin-film resonator used as the sensing element may be formed to support either longitudinal or shear bulk-acoustic wave resonant modes. Preferably, the sensing element is formed to support shear bulk-acoustic wave resonant modes, as they are more suitable for use in a liquid sample.

Additional details regarding sensor devices and systems that may employ TFRs are described in, for example, U.S. Pat. No. 5,932,953 issued Aug. 3, 1999 to Drees et al., which patent is hereby incorporated herein by reference in its entirety to the extent that it does not conflict with the disclosure presented herein.

TFR sensors may be made in any suitable manner and of any suitable material. By way of example, a resonator may include a substrate such as a silicon wafer or sapphire, a Bragg mirror layer or other suitable acoustic isolation means, a bottom electrode, a piezoelectric material, and a top electrode.

Any suitable piezoelectric material may be used in a TFR. Examples of suitable piezoelectric substrates include lithium tantalate (LiTaO$_3$), lithium niobate (LiNbO$_3$), Zinc Oxide (ZnO), aluminum nitride (AlN), plumbum zirconate titanate (PZT) and the like.

Electrodes may be formed of any suitable material, such as aluminum, tungsten, gold, titanium, molybdenum, or the like. Electrodes may be deposited by vapor deposition or may be formed by any other suitable process.

Figure 2:
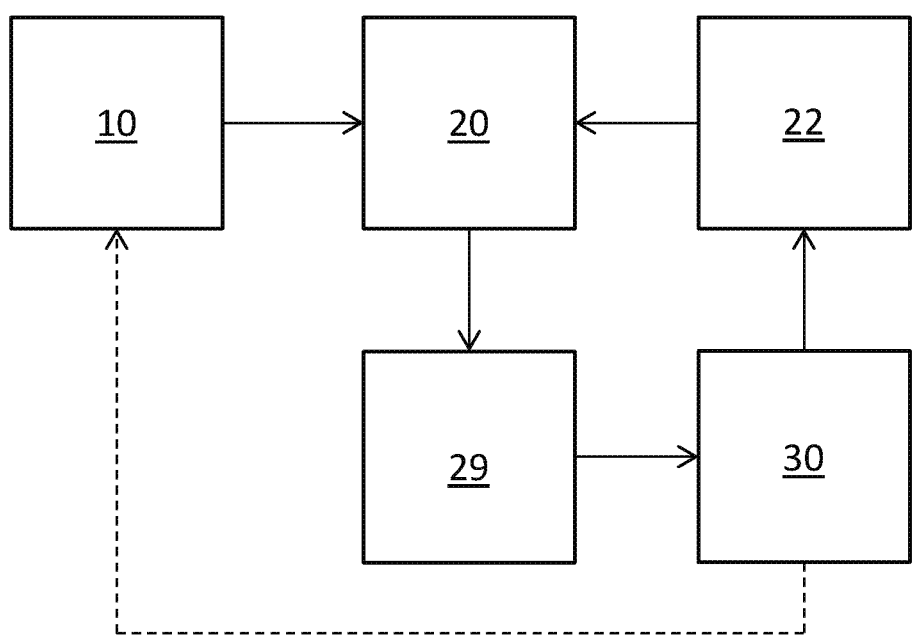
FIG. 2 is a schematic diagram showing components of a BAW system for detecting an analyte.

Any suitable device or system may employ a thin film resonator as described herein. By way of example and with reference to FIG. 2, a system or apparatus for detecting an analyte may include a container 10 (or more than one container), the thin film resonator 20, actuation circuitry 22, measurement circuitry 29, and control electronics or a controller 30. A fluid path couples the one or more containers 10 to the resonator 20. The control electronics 30 are operably coupled to the actuation circuitry and the measurement circuitry. In embodiments, control electronics 30 are configured to modify the frequency at which the actuation circuitry 22 oscillates the resonator 20 based on input from the measurement circuitry 29.

Any suitable control electronics or controller 30 may be employed. For example, control electronics may include a processor, controller, memory, or the like. Memory may include computer-readable instructions that, when executed by processor or controller cause the device and control electronics to perform various functions attributed to device and control electronics described herein. Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Control electronics 30 may include any one or more of a microprocessor, a controller, a digital signal processor (DSP), an application specific integrated circuit (ASIC), a field-programmable gate array (FPGA), or equivalent discrete or integrated logic circuitry. In some examples, control electronics 30 may include multiple components, such as any combination of one or more microprocessors, one or more controllers, one or more DSPs, one or more ASICs, or one or more FPGAs, as well as other discrete or integrated logic circuitry. The functions attributed to control electronics herein may be embodied as software, firmware, hardware or any combination thereof.

Figure 3A:
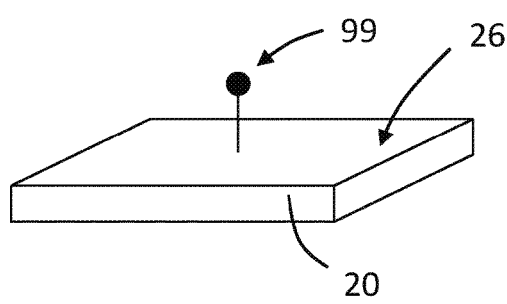
FIGS. 3A-B are schematic diagrams of an embodiment of a first binding partner bound to a surface of a BAW sensor (3A) and a recognition component bound to a second binding partner, which is bound to the first binding partner (3B).
Figure 3B:
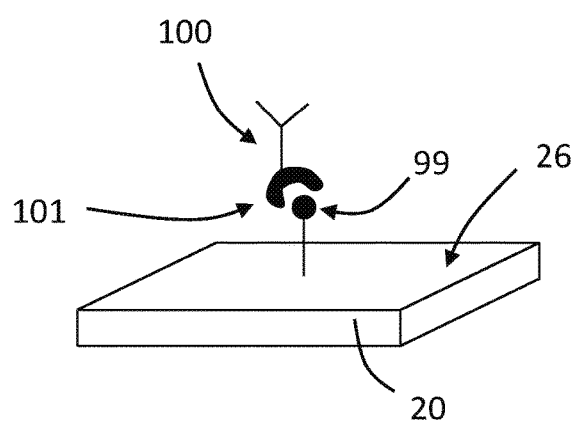

Referring now to FIGS. 3A-B, a first molecular recognition component 100 may be bound to a surface 26 of a BAW sensor 20 via one or more intermediates. For example, a first binding partner 99 may be bound to the surface 26 and the first molecular recognition component 100 may include a second binding partner 101 configured to selectively bind to the first binding partner 99. First recognition component 100 may be bound to surface 26 via binding partners 99, 101 at any suitable time, such as before the sensor 20 is incorporated into a device or system or after the sensor 20 is incorporated into the device or system. For example, first recognition component 100 may be bound to surface 26 via binding partners 99, 101 as a first step of, or during, an analyte detection assay.

Figure 4:
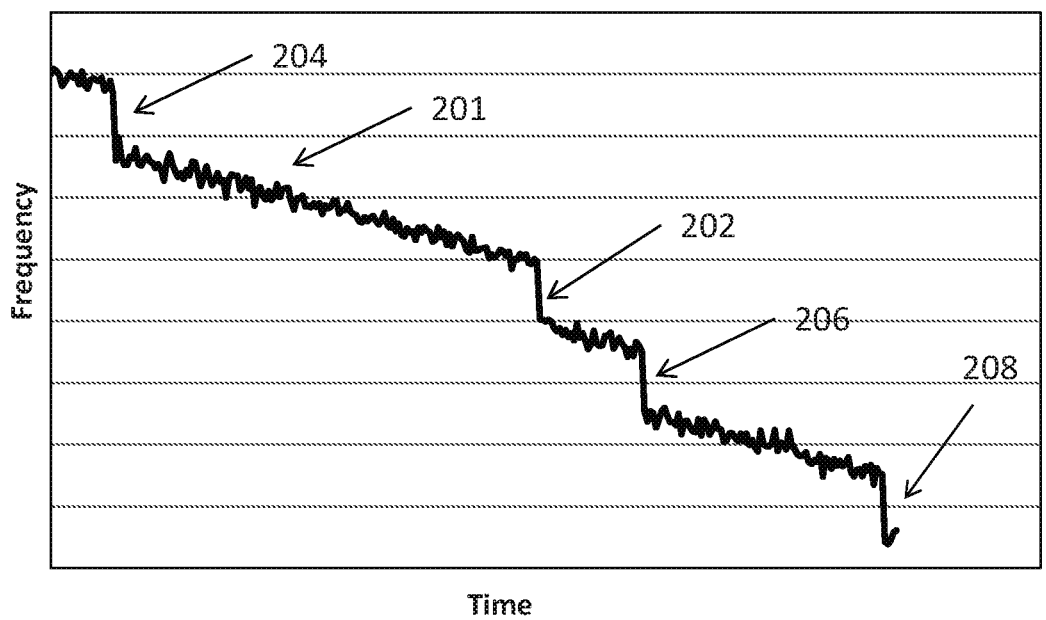
FIG. 4 is a representative curve showing the frequency of a resonance point of a BAW sensor over time as molecules are binding.
Figure 5:
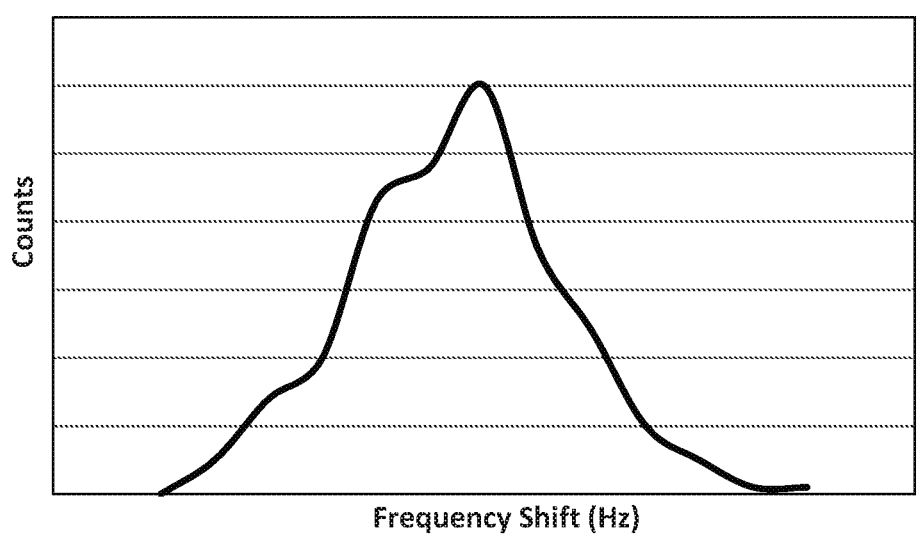
FIG. 5 is a representative curve of a frequency shift spectrum associated with multiple binding events of an analyte to a BAW sensor.

One or more embodiments of systems and apparatuses described herein can be utilized to detect an individual binding event between a molecule of an analyte material and a binding site of a sensing resonator of the apparatus. In one or more embodiments, such apparatus can be utilized to determine a binding rate of the analyte material, e.g., by counting individual binding events. By way of example, FIG. 4 shows a representative curve of the frequency of a resonance point of a sensor over time in such apparatus. One or more embodiments of an apparatus can discriminate between binding and non-binding sources, e.g., by determining a frequency shift of the sensing resonator caused by the individual binding event. For example, section 202 of the curve in FIG. 4 shows the frequency shift caused by the individual binding event. Sections 204, 206, and 208 also show frequency shifts caused by individual binding events. Further, for example, in one or more embodiments, slow drift sources, as indicated by section 201 of the curve in FIG. 4, can be filtered out by analyzing such frequency shifts. Further, in one or more embodiments, an apparatus can discriminate between different binding events (i.e. specific and non-specific) through a frequency shift spectrum of all individual binding events. FIG. 5 shows a representative curve of such a frequency shift spectrum of individual binding events of an analyte to a resonant sensor. The peak and spread of such a spectrum is unique to analytes of different mass and size.

The following equations can be utilized to detect individual binding events:

Simplified Binding Equation $d/dt[\text{Bound}]_{surface}B_0 - \text{Bound}]_{surface}[\text{Sample}]k_a$ if $[\text{Bound}]_{surface}$ is $<<[B_0]_{surface}$:

$d/dt[\text{Bound}]_{surface}B_0]_{surface}[\text{Sample}]k_a,$

Where $B_0$ is an unbound surface antibody at the start of binding (i.e., the surface is 100% unbound at the beginning of the process);

"Bound" is a surface antibody bound to an antigen;

"Sample" is the sample containing the antigen to be measured;

$k_a$ is the on-rate of the antibody-antigen pair;

[ ] represents a volume concentration; and

[ ]$_{surface}$ represents a surface concentration.

Sauerbrey Equation $$\Delta f = -\frac{2f_0^2}{A\sqrt{\rho_q \mu_q}} \Delta m.$$

From these equations, the following can be observed:

(1) Frequency shift is dependent on binding density ($\Delta m/A=[Bound]_{surface}$) and is independent of resonator active area (A) for a given coating density;

(2) The inverse of resonator area (1/A) acts like the gain. As area decreases, frequency shift/mass goes up;

(3) If resonator area is sufficiently reduced, an individual binding event can be detected as a discrete frequency shift above the system noise/drift. This would be a single-molecule detector. Individual binding events can be counted over time, and the rate of such binding events can be related back to the concentration of the sample;

(4) Binding events can produce a rapid frequency shift that can be easily distinguished from slower components produced, e.g., by temperature, fluid shear, or others;

(5) Since the frequency shift associated with each individual binding event is still proportional to mass, if total noise is low enough, a binding spectrum (counts vs. frequency shift) can be constructed that can further distinguish between different types of binding events (i.e. non-specific binding vs. specific binding). For example, a non-specific serum protein binding may bind with a larger average shift than the target binding event. If there is enough statistical separation, the non-specific binding could be separated out from the specific binding. This technique can also be used to correct double-counts that might occur during dead-time;

(6) At small resonator areas and low concentrations, binding events per minute will be extremely low and one resonator alone may not record any or enough events within a reasonable capture time. Arrays can be constructed from individual resonators to create a large enough aggregate detector area to count sufficient binding events during the allotted capture time. Each individual resonator in the array can be independently driven and measured. In this case, detection limit scales with array size. The larger the array, the lower the detection limit, provided the readout electronics are capable of interrogating the array fast enough. (This assumes that non-specific binding can be effectively managed);

(7) Adaptive readout schemes may be utilized that read a small number of resonators extremely quickly when event rates are high (e.g., for high concentration samples), and a large number of resonators more slowly when event rates are low (e.g., low concentration samples).

The size of a capture antibody can be estimated at 15 nm×15 nm×3 nm (Thermo Fisher Application note D19559). It can be immobilized on a flat surface 100% oriented (footprint=15 nm×3 nm) or 100% non-oriented (footprint=15 nm×15 nm), or more typically something in between.

Binding saturation on aluminum nitride 2 GHz BAW shear mode devices is typically on the order of 750 kHz for direct binding (this is antigen dependent). Device improvements to the BAW suggest that the mass sensitivity can be improved up to 10 fold. In this case, it would be expected to saturate near 7.5 MHz.

The level of orientation of antibody immobilization on the BAW surface and the packing density of the bound antigen may be unknown. However, the antibody coating should fall between the 100% oriented surface and 100% non-oriented surface. These conditions can be used as an upper and lower bound to estimate the active area of the BAW resonator needed to detect single binding events.

|  | Non-oriented, Low Density (15 nm x 15 nm footprint) | Oriented, High Density (15 nm x 3 nm footprint) |
|---|---|---|
| Current Device | | |
| Saturation Shift (Hz) | 750000 | 750000 |
| 500 Hz Binding Event — Total Binding Sites | 1500 | 1500 |
| 500 Hz Binding Event — Active Area ($\mu m^2$) | 0.3375 | 0.0675 |
| 100 Hz Binding Event — Total Binding Sites | 7500 | 7500 |
| 100 Hz Binding Event — Active Area ($\mu m^2$) | 1.6875 | 0.3375 |
| Improved Device | | |
| Saturation Shift (Hz) | 7500000 | 7500000 |
| 500 Hz Binding Event — Total Binding Sites | 15000 | 15000 |
| 500 Hz Binding Event — Active Area ($\mu m^2$) | 3.375 | 0.675 |
| 100 Hz Binding Event — Total Binding Sites | 75000 | 75000 |
| 100 Hz Binding Event — Active Area ($\mu m^2$) | 16.875 | 3.375 |

The approximate resonator area needed to operate in binding event counting mode based on the total shift desired per event to overcome system noise can be estimated. Two different frequency shift thresholds can be used: 500 Hz and 100 Hz. The current BAW device can be capable of counting binding events if the active area is approximately 1 $\mu m^2$. The improved BAW device can be capable of counting binding events if the active area is approximately 4-17 $\mu m^2$.

Since at these extremely small device areas binding events will be rare at low analyte concentrations, an array may be needed to increase the effective detection area. Each BAW resonator in the array is capable of counting binding events independently, and the events from each BAW resonator are summed to generate a total for the array. The count rate for a 256 element array is estimated as a function of analyte concentration. Using the current BAW response of 10 ng/ml rTSH in a buffer/BSA solution of approximately 5 kHz/min responses (in binding events/min) can be estimated for BAW devices with an area of 1.7 $\mu m^2$.

| Current Sensor | | | | |
|---|---|---|---|---|
| Sample Concentration (ng/ml) | Response (Hz/min) | Response (Fractional Saturation/min) | Events/min (Single BAW A = 1.7 $\mu m^2$) | Events in 10 min. (Single BAW A = 1.7 $\mu m^2$) | 256 Array Total Events in 10 min. |
| 10 | 5000 | 0.0066667 | 50.00 | 500 | 128000 |
| 1 | 500 | 0.0006667 | 5.00 | 50 | 12800 |
| 0.1 | 50 | 0.0000667 | 0.50 | 5 | 1280 |
| 0.01 | 5 | 0.0000067 | 0.05 | 0.5 | 128 |
| 0.001 | 0.5 | 0.0000007 | 0.01 | 0.05 | 12.8 |
| Improved Sensor (approx. 10x mass sensitivity) | | | | | |
| Sample Concentration (ng/ml) | Response (Hz/min) | Response (Fractional Saturation/min) | Events/min (Single BAW A = 17 $\mu m^2$) | Events in 10 min. (Single BAW A = 17 $\mu m^2$) | 256 Array Total Events in 10 min. |
| 10 | 50000 | 0.0066667 | 500.00 | 5000 | 1280000 |
| 1 | 5000 | 0.0006667 | 50.00 | 500 | 128000 |
| 0.1 | 500 | 0.0000667 | 5.00 | 50 | 12800 |
| 0.01 | 50 | 0.0000067 | 0.50 | 5 | 1280 |
| 0.001 | 5 | 0.0000007 | 0.05 | 0.5 | 128 |

In one aspect, the present disclosure provides an apparatus for measuring binding kinetics of an interaction of an analyte material present in a fluid sample. The apparatus includes a sensing resonator having at least one binding site for the analyte material. Any suitable sensing resonator can be utilized. Further, any suitable number of sensing resonators can be utilized. In one or more embodiments, the sensing resonator can include an array of sensing resonators. In one or more embodiments, the sensing resonator is a bulk acoustic wave resonator that can include a resonant frequency of at least 900 MHz and no greater than 10 GHz. In one or more embodiments, the sensing resonator is of sufficiently small mass for the controller to detect the individual binding event. As used herein, the term "sufficiently small" means that the device area is selected to be small enough to provide a measureable frequency shift above the noise level due to a single binding event. In one or more embodiments, the mass of the sensing resonator can be reduced to increase the sensitivity of the apparatus.

The apparatus also includes actuation circuitry adapted to drive the sensing resonator into an oscillating motion. Any suitable actuation circuitry can be utilized, e.g., the actuation circuitry described herein. In one or more embodiments, the actuation circuitry can be adapted to individually drive each resonator of an array of resonators at the same or different frequencies of one or more additional resonators.

The apparatus can also include measurement circuitry coupled to the sensing resonator and adapted to measure an output signal of the sensing resonator representing resonance characteristics of the oscillating motion of the sensing resonator. Any suitable measurement circuitry can be utilized, e.g., the measurement circuitry described herein. In one or more embodiments, the measurement circuitry can be adapted to individually measure an output signal of each sensing resonator of an array of sensing resonators. In one or more embodiments, the apparatus can include an array of sensing resonators each including at least one binding site for the analyte material, where the measurement circuitry is adapted to measure an output signal of each sensing resonator of the array of sensing resonators that represents resonance characteristics of the oscillating motion of the respective sensing resonator.

The apparatus can also include a controller coupled to the actuation and measurement circuitry, where the controller is adapted to detect an individual binding event between the at least one binding site and a molecule of the analyte material. The controller can be further adapted to perform one or more of the following:

determine the frequency at which the actuation circuitry drives the sensing resonator;

detect the individual binding event by determining a first frequency of the output signal of the sensing resonator prior to the binding event and a second frequency of the output signal following the individual binding event;

detect the individual binding event by determining a frequency shift of the output signal of the sensing resonator based upon the first frequency and the second frequency;

detect the individual binding event by comparing the frequency shift to a frequency shift threshold. The threshold can be any suitable value. In one or more embodiments, the frequency shift can be compared to a lower threshold and an upper threshold, i.e., individual binding events can be associated with a frequency shift that is at greater than or equal to a lower limit and less than or equal to an upper limit. Such comparison to one or both of a lower and upper limit can aid in filtering out non-binding events;

determine a binding rate of the analyte material;

determine the binding rate of the analyte material by counting a number of individual binding events per unit time; and determine a concentration of the analyte material based upon the binding rate of the analyte material.

The apparatus can also include one or more reference resonators coupled to the actuation circuitry and the measurement circuitry. Any suitable reference resonator can be included, e.g., the reference resonators described herein. In one or more embodiments, the reference resonator is free of binding sites of the analyte material. In one or more embodiments, the actuation circuitry is adapted to independently drive the reference resonator and the sensing resonator into oscillating motion.

Any suitable technique or combination of techniques can be utilized with the systems and apparatuses described herein to measure the binding kinetics of an interaction of an analyte material present in a fluid sample and, e.g., to detect an individual binding event. In one or more embodiments, a sensing resonator can be contacted with the fluid sample, where the sensing resonator includes at least one binding site for the analyte material. The sensing resonator can be actuated into an oscillating motion. An output signal representing resonance characteristics of the oscillating motion of the sensing resonator can be measured. Further, an individual binding event between the at least one binding site and a molecule of the analyte material can be detected. In one or more embodiments, detecting the individual binding event can include detecting a frequency shift of the output signal of the sensing resonator.

In one or more embodiments, the frequency shift of the output signal can be detected by determining a first frequency of the output signal of the sensing resonator prior to the binding event; determining a second frequency of the output signal of the sensing resonator following the individual binding event; and comparing the first frequency to the second frequency. In one or more embodiments, the frequency shift representative of one or more subsequent binding events can be detected using any suitable technique or combination of techniques.

In one or more embodiments, the method can also include contacting a reference resonator with the fluid sample, wherein the reference resonator is free of binding sites for the analyte material; actuating the reference resonator into an oscillating motion; and measuring an output signal representing resonance characteristics of the oscillating motion of the reference resonator.

In one or more embodiments, the method can also include comparing the output signal of the sensing resonator to the output signal of the reference resonator.

In one or more embodiments, the method can include determining a binding rate of the analyte material. In one or more embodiments, the binding rate can be determined by counting a number of individual binding events per unit time. For example, in one or more embodiments, a number of individual binding invents that cause a first frequency shift can be counted, and a number of individual binding invents that cause a second frequency shift can also be counted. Additional counts of third, fourth, fifth, etc., frequency shifts can be counted, and a histogram or spectrum of counts of individual binding invents versus frequency shifts or bands can be formulated. In one or more embodiments, a particular analyte can exhibit a unique or characteristic histogram such that the particular analyte can be determined based upon the histogram provided by the apparatus. In one or more embodiments, a particular analyte can exhibit a unique or characteristic histogram such that only binding events corresponding to that particular analyte are used to determine a binding rate.

Use

The sensors, devices, and systems described herein may be employed to detect an analyte in a sample. The sensors may find use in numerous chemical, environmental, food safety, or medical applications. By way of example, a sample to be tested may be acquired or may be derived from blood, serum, plasma, cerebrospinal fluid, saliva, urine, and the like. Other test compositions that are not fluid compositions may be dissolved or suspended in an appropriate solution or solvent for analysis.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

"Binding event," as used herein, means the binding of a target analyte to a molecular recognition component immobilized in a surface of a sensor.

Thus, embodiments of A RESONATOR FOR DETECTING SINGLE MOLECULE BINDING are disclosed. One skilled in the art will appreciate that the devices such as signal generators, systems, and methods described herein can be practiced with embodiments other than those disclosed. The disclosed embodiments are presented for purposes of illustration and not limitation. One will also understand that components of the leads depicted and described with regard the figures and embodiments herein may be interchangeable.

What is claimed is:

1. An apparatus for measuring binding kinetics of an interaction of an analyte material present in a fluid sample, comprising:
    a sensing resonator comprising at least one binding site for the analyte material;
    actuation circuitry adapted to drive the sensing resonator into an oscillating motion;
    measurement circuitry coupled to the sensing resonator and adapted to measure an output signal of the sensing resonator representing resonance characteristics of the oscillating motion of the sensing resonator; and
    a controller coupled to the actuation and measurement circuitry, wherein the controller is adapted to detect an individual binding event between the at least one binding site and a molecule of the analyte material.

2. The apparatus of claim 1, wherein the controller is further adapted to determine the frequency at which the actuation circuitry drives the sensing resonator.

3. The apparatus of claim 1, wherein the controller is further adapted to detect the individual binding event by determining a first frequency of the output signal of the sensing resonator prior to the binding event and a second frequency of the output signal following the individual binding event.

4. The apparatus of claim 3, wherein the controller is further adapted to detect the individual binding event by determining a frequency shift of the output signal of the sensing resonator based upon the first frequency and the second frequency.

5. The apparatus of claim 4, wherein the controller is further adapted to detect the individual binding event by comparing the frequency shift to a frequency shift threshold.

6. The apparatus of claim 1, further comprising a reference resonator free of binding sites for the analyte material, wherein the reference resonator is coupled to the actuation circuitry and the measurement circuitry.

7. The apparatus of claim 6, wherein the actuation circuitry is adapted to independently drive the reference resonator and the sensing resonator into oscillating motion.

8. The apparatus of claim 1, wherein the sensing resonator is a bulk acoustic wave resonator comprising a resonant frequency of at least 900 MHz and no greater than 10 GHz.

9. The apparatus of claim 1, wherein the sensing resonator is of sufficiently small mass for the controller to detect the individual binding event.

10. The apparatus of claim 1, wherein the controller is further adapted to determine a binding rate of the analyte material.

11. The apparatus of claim 10, wherein the controller is adapted to determine the binding rate of the analyte material by counting a number of individual binding events per unit time.

12. The apparatus of claim 10, wherein the controller is further adapted to determine a concentration of the analyte material based upon the binding rate of the analyte material.

13. The apparatus of claim 1, wherein the sensing resonator comprises an array of sensing resonators each comprising at least one binding site for the analyte material, wherein the measurement circuitry is adapted to measure an output signal of each sensing resonator of the array of sensing resonators that represents resonance characteristics of the oscillating motion of the respective sensing resonator.

* * * * *